United States Patent
Berg

[11] Patent Number: 5,961,789
[45] Date of Patent: Oct. 5, 1999

[54] SEPARATION OF T-AMYL ALCOHOL FROM N-BUTANOL BY EXTRACTIVE DISTILLATION

[76] Inventor: Lloyd Berg, 1314 S. 3rd Ave., Bozeman, Mont. 59715

[21] Appl. No.: 09/032,824

[22] Filed: Mar. 2, 1998

[51] Int. Cl.⁶ .............................. B01D 3/40; C07C 29/84
[52] U.S. Cl. ................ 203/57; 203/58; 203/59; 203/60; 203/62; 203/63; 203/64; 568/913
[58] Field of Search ................ 203/57, 58, 59, 203/60, 63, 64, 62; 568/913

[56] References Cited

U.S. PATENT DOCUMENTS

| | | | |
|---|---|---|---|
| 2,551,584 | 5/1951 | Carlson et al. | 203/51 |
| 2,559,519 | 7/1951 | Smith et al. | 203/64 |
| 2,570,205 | 10/1951 | Carlson et al. | 203/58 |
| 2,595,805 | 5/1952 | Morrell et al. | 203/84 |
| 4,366,032 | 12/1982 | Mikitenko et al. | 203/58 |
| 4,428,798 | 1/1984 | Zud Kevitch et al. | 203/65 |
| 4,693,787 | 9/1987 | Berg et al. | 568/913 |
| 4,693,788 | 9/1987 | Berg et al. | 203/57 |
| 4,756,803 | 7/1988 | Berg | 203/60 |
| 4,877,530 | 10/1989 | Moses | 203/43 |
| 4,935,103 | 6/1990 | Berg et al. | 203/60 |
| 5,360,520 | 11/1994 | Berg | 203/57 |
| 5,718,809 | 2/1998 | Berg | 203/62 |
| 5,756,866 | 5/1998 | Rescalli et al. | 568/913 |
| 5,772,853 | 6/1998 | Berg | 203/65 |
| 5,879,517 | 3/1999 | Berg | 203/59 |
| 5,904,815 | 5/1999 | Berg | 203/57 |

*Primary Examiner*—Virginia Manoharan

[57] ABSTRACT

T-Amyl alcohol cannot be separated from n-butanol by distillation or rectification because of the closeness of their boiling points. T-Amyl alcohol is readily separated from n-butanol by extractive distillation. Effective agents are dimethylsulfoxide, N.N.dimethyl formamide and ethanolamine.

1 Claim, No Drawings

SEPARATION OF T-AMYL ALCOHOL FROM N-BUTANOL BY EXTRACTIVE DISTILLATION

FIELD OF THE INVENTION

This invention relates to a method for separating t-amyl alcohol from n-butanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | |
|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 | t-Amyl alcohol and n-butanol boil sixteen degrees apart and have a relative volatility of 1.25 which makes it difficult to separate them by conventional distillation or rectification. Table 2 shows that with an agent giving a relative volatilty of 1.5, only 30 actual plates are required to get 99% purity compared to 55 plates for straight rectification.

TABLE 2

Theoretical and Actual Plates Required vs. Relative Volatility for t-Amyl Alcohol From n-Butanol Separation

| Relative Volatility | Theoretical Plates Required At Total Reflux, 99% Purity | Actual Plates Required, 75% Efficiency |
|---|---|---|
| 1.25 | 41 | 55 |
| 1.4 | 26 | 35 |
| 1.5 | 22 | 30 |

OBJECTIVE OF THE INVENTION

The object of this invention is to provide a process or method of extractive distillation that will enhance the relative volatility of t-amyl alcohol and n-butanol in their separation in a rectification column. It is a further object of this invention to identify effective extractive distillation agents that are stable and can he recycled.

SUMMARY OF THE INVENTION

The objects of this invention are provided by a process for the separation of t-amyl alcohol from n-butanol which entails the use of certain organic compounds when employed as the agent in extractive distillation.

DETAILED DESCRIPTION OF THE INVENTION

I have discovered that certain organic compounds will effectively increase the relative volatility between t-amyl alcohol and n-butanol during rectification when employed as the agent in extractive distillation. They are 2-methoxyacetophenone, pyridine, ethylene diamine, morpholine, N,N-dimethylethanolamine, ethanolamine, dipropylamine, hexamethylenediamine, bis-(hexamethylene)triamine, 1,3-pentanediamine, hexamethyleneimine, 2-methylpentamethylenediamine. dimethylsulfoxide, 2-pyrrolidinone, 1-methylpiperazine, N-methylpyrrolidinone, 1-(2-hydroxyethyl)-2-pyrrolidinone, tetraethylorthosilicate, triacetin, formamide, tripropyleneglycolmethylether, 3-methylaminopropylamine, 1-methyl-2-pyrrolidinone, 2-methoxyethanol, N,N-dimethylformamide, N,N-dimethylacetamide, diethyleneglycolmethylether, diethyleneglycolethylether 1,2-propanediol, 5-methyl-2-hexanone, diethylmalonate and 2-methyl-2,4-pentanediol.

THE USEFULNESS OF THE INVENTION

The usefulness of this invention can be demonstrated by referring to the data presented in Tables 1, 2 and 3. All of the successful agents show that t-amyl alcohol can be separated from n-butanol by means of extractive distillation in a rectification column and that the ease of separation as measured by relative volatility is considerable.

TABLE 3

Effective Extractive Distillation Agents For Separating t-Amyl Alcohol From n-Butanol

| Compounds | Relative Volatility |
|---|---|
| None | 1.25 |
| 2-Methoxyacetophenone | 1.35 |

TABLE 3-continued

Effective Extractive Distillation Agents For
Separating t-Amyl Alcohol From n-Butanol

| Compounds | Relative Volatility |
| --- | --- |
| Pyridine | 1.4 |
| Ethylene diamine | 2.0 |
| Morpholine | 1.45 |
| N,N-Dimethylethanolamine | 1.4 |
| Ethanolamine | 1.7 |
| Dipropylamine | 1.45 |
| Hexamethylenediamine | 1.6 |
| Bis-(Hexamethylene)triamine | 1.6 |
| 1,3-Pentanediamine | 1.75 |
| Hexamethyleneimine | 1.5 |
| 2-Methylpentamethylenediamine | 1.55 |
| Dimethylsulfoxide | 1.7 |
| 2-Pyrrolidinone | 1.55 |
| 1-Methylpiperazine | 1.65 |
| N-Methylpyrrolidinone | 1.6 |
| 1-(2-Hydroxyethyl)-2-pyrrolidinone | 1.6 |
| Tetraethylorthosilicate | 1.4 |
| Triacetin | 1.35 |
| Formamide | 1.5 |
| Tripropyleneglycolmethylether | 1.5 |
| 3-Methylaminopropylamine | 1.7 |
| 1-Methyl-2-pyrrolidinone | 1.45 |
| N,N-Dimethylformamide | 1.6 |
| 2-Methoxyethanol | 1.4 |
| N,N-Dimethylacetamide | 1.6 |
| Diethyleneglycolmethylether | 1.4 |
| Diethyleneglycolethylether | 1.45 |
| 1,2,Propanediol | 1.5 |
| 5-Methyl-2-hexanone | 1.4 |
| Diethylmalonate | 1.9 |
| 2-Methyl-2,4-pentanediol | 1.5 |

WORKING EXAMPLE

1. Fifty grams of t-amyl alcohol—n-butanol mixture and fifty grams of dimethylsulfoxide were charged to a vapor—liquid equilibrium still and refluxed for two hours. The vapor composition was 25.5% t-amyl alcohol and 74.5% n-butanol. The liquid composition was 16.5% t-amyl alcohol and 83.5%6 n-butanol. This is a relative volatility of 1.7.

I claim:

1. A method for recovering t-amyl alcohol from a mixture of t-amyl alcohol and n-butanol which consists essentially of distilling a mixture consisting of t-amyl alcohol and n-butanol in the presence of an extractive agent, recovering the t-amyl alcohol as overhead product and obtaining the n-butanol and the extractive agent as bottoms product, wherein said extractive agent consists essentially of one material selected from the group consisting of pyridine, ethylene diamine, morpholine, N,N-dimethylethanolamine, ethanolamine, dipropylamine, hexamethylenediamine, bis-(hexamethylene)triamine, 1,3-pentanediamine, hexamethyleneimine, 2-methylpentamethylenediamine. dimethylsulfoxide, 2-pyrrolidinone, 1-methylpiperazine, N-methylpyrrolidinone, 1-(2-hydroxyethyl)-2-pyrrolidinone, tetraethylorthosilicate, triacetin, formamide, tripropyleneglycolmethylether, 3-methylaminopropylamine, 1-methyl-2-pyrrolidinone, 2-methoxyethanol, N,N-dimethylformamide, N,N-dimethylacetamide, diethyleneglycolmethylether, diethyleneglycolethylether 1,2-propanediol, 5-methyl-2-hexanone, diethylmalonate, 2-methyl-2,4-pentanediol and 2-methoxyacetophenone.

* * * * *